United States Patent [19]

Thompson

[11] 4,076,021
[45] Feb. 28, 1978

[54] POSITIVE PRESSURE RESPIRATORY APPARATUS

[76] Inventor: Harris A. Thompson, 175 Bellevue Drive, Boulder, Colo. 80302

[21] Appl. No.: 709,450

[22] Filed: Jul. 28, 1976

[51] Int. Cl.$^2$ ............................................. A61M 16/00
[52] U.S. Cl. ................................. 128/145.6; 92/13.7; 92/13 R
[58] Field of Search ............... 128/145.6, 145.7, 145.8, 128/145.5, 142 R, 142.3, 202, 203, 188; 92/13.7, 13 R

[56] References Cited

U.S. PATENT DOCUMENTS

| | | | |
|---|---|---|---|
| 2,841,991 | 7/1958 | Saalfrank | 92/13.7 |
| 3,087,707 | 4/1963 | Seeler | 128/145.8 |
| 3,613,677 | 10/1971 | Blasko | 128/145.6 |
| 3,651,804 | 3/1972 | Spiller | 128/145.6 |
| 3,818,806 | 6/1974 | Fumagalli | 92/13.7 |

Primary Examiner—Stephen C. Pellegrino
Assistant Examiner—Henry J. Recla
Attorney, Agent, or Firm—Van Valkenburgh and Lowe

[57] ABSTRACT

This invention is a positive pressure respiratory apparatus to cyclically pump proper volumes of air for inspiration by a patient, through a breathing tube extended to the patient. The unit, formed in a compact package, includes a pump, a piston within a cylinder and a breathing tube extending from the cylinder to the patient. The cylinder volume does not greatly exceed the proper volume of air for inspiration by a patient. The piston is cyclically reciprocated within the cylinder at a rate which corresponds to natural or selected inspiration and exhalation breathing cycles of the patient, and this piston moves in the cylinder a distance sufficient to displace the aforesaid volume of air. A valving means permits air to enter the cylinder during the patient's exhalation cycle of breathing when the piston moves away from the cylinder end and to confine the flow of air to the breathing tube during the inspiration cycle, when the piston moves towards the cylinder end wall.

This unit is adapted to operate on a common 110 volt A.C. current supply or upon batteries. The power consumption is minimal, so that the unit may operate for as long as 24 hours on a storage battery and as long as an hour on a few small flashlight batteries conveniently carried in the case of the unit. This permits the apparatus to continue to operate even when the user is taking short trips where he is away from his regular power source.

5 Claims, 19 Drawing Figures

POSITIVE PRESSURE RESPIRATORY APPARATUS

The present invention relates to artificial respiration apparatus, and more particularly to portable positive pressure artificial respiration apparatus of the general type which is disclosed in my U.S. Pat. No. 3,094,274 issued June 18, 1963.

That patent discloses an apparatus using a blower for a continuous airflow which is valved to be cyclically directed to the patient during inspiration and to be exhausted to the atmosphere during expiration. The continuous-flow respiration apparatus, which can be packaged in a small case, was developed to avoid the bulky, heavy piston types of artificial respiration apparatus then in use. That piston type apparatus was commonly associated with iron lungs and heavy equipment which was not portable.

Over the years it has been recognized that certain disadvantages existed with the continuous respiration apparatus. The continuous airflow requires far more energy than is actually necessary to assist a patient in breathing. Such energy requirements for such operations are not significant whenever a conventional, 110 volt, alternating current power source is available. However, the energy demand does become critical whenever the respirator must use storage batteries to power the blower, as in an emergency or under other circumstances when the 110 volt A.C. power source is not available and the battery operation of the artificial respiration apparatus must continue for a significant period of time. Storage batteries not only require recharging, but they are quite bulky and heavy and they are good for only a few hours of use. Thus, the apparatus, although packaged in a small, compact container, is still, for practical purposes, non-portable unless the storage batteries are included.

The use of positive pressure respiration apparatus has increased substantially over the years because of the realization that many breathing problems, such as emphysema and asthma, can be helped by this apparatus. Other situations such as partial paralysis render the apparatus essential. Because of this, more widespread use of such apparatus, there is an ever increasing desire for a truly portable unit. There is also an increasing need for a simpler, lighter apparatus and one which can operate for a period of time without either heavy storage batteries or a standard 110 volt A.C. current power source.

The present invention was conceived and developed with such a need in view and this invention comprises, in essence, a positive pressure respiration apparatus which is a pump type, but of a compact, simplified, light-weight arrangement, and which is packaged in a comparatively small case. It was discovered that this improved respiration apparatus uses a surprisingly small amount of power in its operation. Thus, a group of small, rechargeable batteries are placed inside the case and are sufficient to permit the apparatus to run for more than one hour. This can keep the apparatus in operation in an emergency and also permits the patient to travel for short periods of time without taking heavy batteries from one location to another.

It follows that a primary object of the invention is to provide a novel and improved positive-pressure breathing apparatus which is a portable, light weight, self-contained unit that may operate with either conventional, 110 volt A.C. power, with 12-volt storage batteries or with small, rechargeable, dry-cell batteries carried within the unit.

Another object of the invention is to provide a novel and improved positive pressure breathing apparatus which precisely controls the breathing operations, including the timing of the breathing cycle, and the volume and pressure of pumped air during each inspiration cycle, and which is easily adjusted to set or modify these variables.

Another object of the invention is to provide a novel and improved apparatus for positive pressure breathing which permits the operator to know the power source being used, the condition of the batteries and the pumping pressures, and which will sound an alarm if the operation is not proper.

Another object of the invention is to provide in conjunction with a positive pressure artificial respiration apparatus, a double-action check valve in the breathing tube which is especially adapted to respond and control the inspiration and expiration cycles of a patient using the apparatus.

Another object of the invention is to provide a novel and improved positive pressure breathing apparatus using a piston-cylinder type air pump which can be adjusted to produce either a constant volume inspiration cycle or a constant pressure inspiration cycle.

Other objects of the invention are to provide a positive pressure breathing apparatus which is simple, neat appearing, economical and rugged and durable.

With the foregoing and other objects in view, my present invention comprises certain constructions, combinations and arrangements of parts and elements as hereinafter described, defined in the appended claims, and illustrated in preferred embodiment by the accompanying drawing in which:

Referring more particularly to the drawing, the respiration apparatus, constructed according to the invention, is carried in a small case C which is approximately 8 inches wide, 8½ inches high and 15 inches long. This case is made of rigid, high quality material such as is used in some types of luggage cases. The case, with a box-like body 20 and a moderately thick lid 21, will be normally closed by latches 22 and is carried by a handle 23. The several components of the positive pressure respiration unit include: the pumping mechanism P which is within the case; a breathing tube 24 extended from a pressure control valve 25 at the front of the case; an exhalation check valve 26 at the end of the breathing tube and a mouthpiece 27 at the check valve for the patient to use as hereinafter further described. Also, an array of operative controls and indicators are mounted at a convenient location on the lid 21 of this case and adjusting controls may be located within the case and are accessible by merely lifting the lid 21. These adjusting controls are above a cover plate 28 within the body and adjacent to the top of the case. The pumping mechanism P, the pressure control valve 25, a ventilator, storage batteries, electrical components and portions of circuit wires are located below this cover plate 28 as will be hereinafter described. Also, some of the circuit wires will extend through an edge opening in this plate 28 to the lid 21 to connect with the operative controls and indicators at the lid. An inner lid cover 29 encloses these wires. Suitable electrical power source leads are connected to this case, from both a 110 volt AC household source and a 12 volt storage battery. These power source leads are connected into the unit as at suitable sockets in the side walls of the case, as illustrated at socket 30.

This general arrangement of these components permits a patient to use the apparatus without opening the lid. He may start, stop and monitor the apparatus by the controls at the top of the lid for there will be suitable gages and indicators to indicate what is occurring during the operation of the unit. Should a patient wish to adjust the apparatus or to adjust the regimen imposed upon him by the apparatus, he has only to open the lid and make adjustments at the knobs exposed above the cover plate 28. The only time it is necessary to remove this cover plate 28 is for maintenance and repair.

The controls at the top of the lid include an off-on switch 31. A two-position switch 32 is provided to operate the unit on either the internal batteries or on an external 12-volt storage battery. An indicator light 33, at one side of the switch 32, is turned on whenever the unit is operating on internal batteries and a corresponding indicator light 34, at the opposite side, is turned on whenever the unit is operating on an external battery. This unit is wired to automatically charge the batteries whenever it is operating on a 110 volt power source and a battery charge indicator 35 is provided on the lid. If the batteries, or the power source being used fails, or begins to fail, or if the respiration pressure drops or increases excessively, an alarm 36 will call the patient's attention to the problem. A pressure gage 37 is also provided at the top of this lid so that the operator will know at all times what the respiration pressure is.

Whenever the lid 21 is opened for adjustment of the apparatus, there will be exposed a rate control knob 38 shown at the underside of the lid, a pressure regulation adjustment 39 above the pressure control valve 25 and a pump-volume adjustment 40, a knob above a slot 41 in the cover plate 28. In addition, the unit will carry sockets for placing the necessary fuses 42 at this cover plate 28.

The components within the box below the cover plate 28 include the pump mechanism P as hereinafter further described, a ventilating fan 43, the pressure control valve 25, suitable storage batteries 44 and various wire leads and electrical components generally indicated at 45, to make up the several circuits of the unit. The circuitry to operate this apparatus is not described in detail herein because once a technician understands the functions of the various components hereinafter described, he will be able to devise adequate circuits for proper operation of these units.

It is to be noted that the interior of the case must be well ventilated to prevent a temperature buildup which will not only cause overheating of the operative components, but will also warm the pumped air to an uncomfortable temperature. The fan 43 is a small exhaust fan mounted at the rear wall of the case to discharge through an opening in this rear wall, which is not shown in the drawing. A number of vent intake openings 46 are also provided in the walls and lid of the unit to permit a continuous inflow of air from several directions to effectively cool the apparatus.

Figures 1, 2, 3, 9, 13, 14:
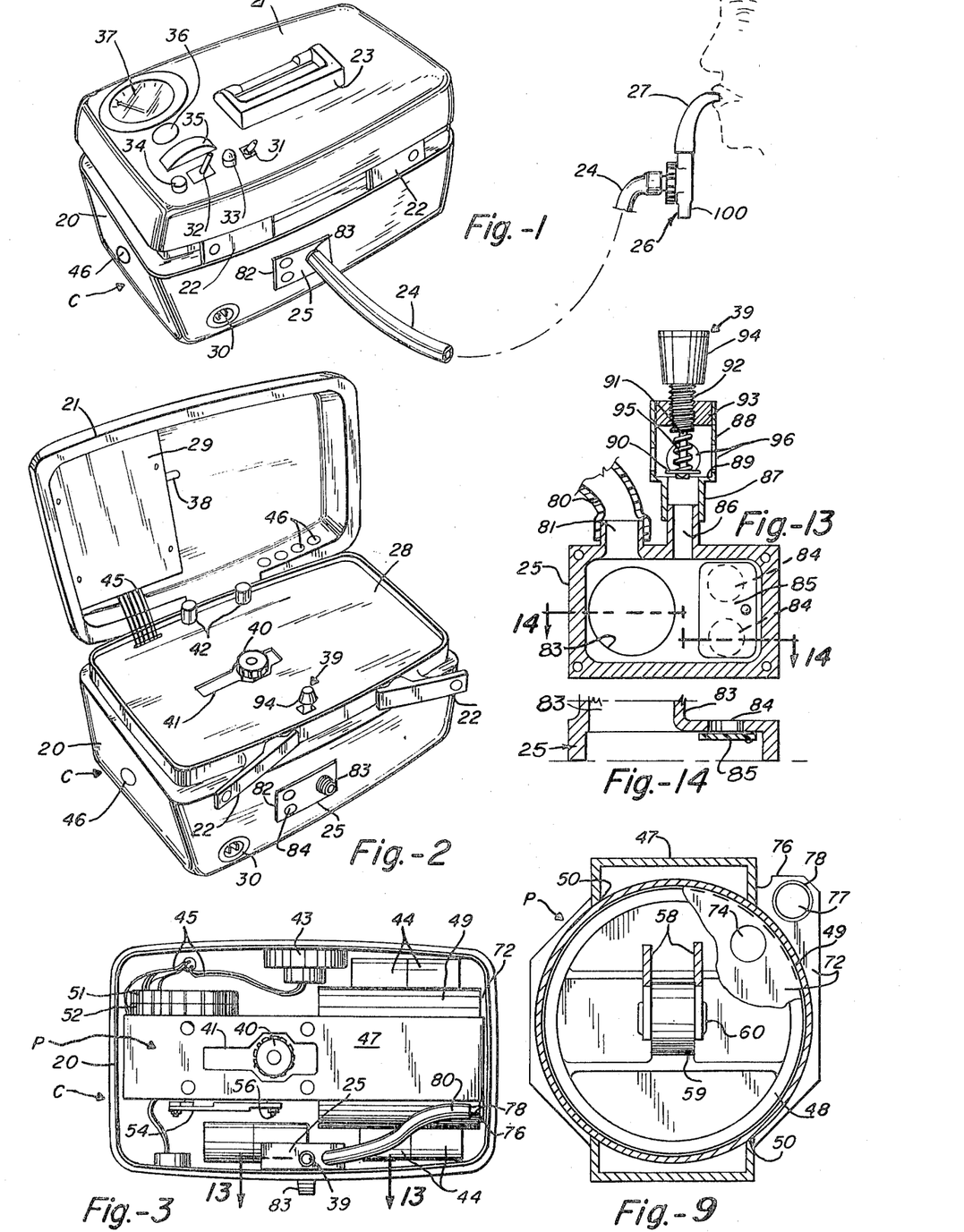
FIG. 1 is a perspective view of a positive pressure respiration apparatus constructed according to the invention, enclosed within a case and including a breathing tube and an improved exhalation valve terminating at the breathing tube.
FIG. 2 is a perspective view of the apparatus with the case being opened to better show controls for several adjustments therein.
FIG. 3 is a plan view of the apparatus shown at FIG. 2, but with the cover plate removed to illustrate the several components within the case.
FIG. 9 is a transverse sectional view as taken from the indicated line 9—9 at FIG. 5, but with portions broken away to show parts otherwise hidden from view.
FIG. 13 is a sectional view of a pressure control chamber in the respiration line, as taken from the indicated line 13—13 at FIG. 3, but on an enlarged scale.
FIG. 14 is a sectional view as taken from the indicated line 14—14 at FIG. 13.

The pump mechanism P is built as a unitized structure adapted to fit snugly within the case C, beneath the cover plate 28 and in a manner such that it can be easily removed for inspection or repair if necessary. This pump mechanism is carried in a framework 47 which is a rectangular tube, preferably of aluminum. This tube has a length of approximately 14 inches, a height of 6 inches and a width of 3 inches, and as such, it will nicely fit into the case body 20 with the cover plate 28 resting upon the top of the framework 47. This framework 47 has a width less than the width of the case to provide space for other components to be stored within the case, such as the batteries 44, as best illustrated at FIG. 3.

The positive pressure breathing action of the apparatus is through pumping, effected by a piston 48 reciprocating within a cylinder 49. The mechanisms constituting the piston drive are adjustable to vary the time and volume of each cyclic stroke of the piston, as will be described. With the proportions of the framework 47 as above noted, a cylinder 49, which is approximately five inches in diameter, can be fitted within a longitudinally disposed socket cutout 50 at one end of the frame 47 and this cylinder 49 need be about half the length of the framework 47 to accommodate sufficient air to permit a full inspiration cycle of breathing by an individual with a very large lung capacity. This will occur whenever the stroke of the piston 48 within the cylinder is at maximum. Shorter strokes will reduce the amount of air pumped each cycle and can be used for smaller individuals. This variation of the piston stroke is accomplished through a suspended rocker R which is mounted within the framework adjacent to the cylinder as will now be described. It is to be noted, however, that the pressure control valve 25 may be used to provide a constant-pressure type of inspiration cycle rather than a fixed-volume type of inspiration, in which case, longer piston strokes will be used with some waste of excess air, as hereinafter described.

A small, comparatively flat, electric motor 51 is mounted at the back side wall of the unit at the end of the framework 47 opposite to the cylinder 49. This motor 50 is combined with a disc-shaped gear reducer 52 to produce a slow rpm output shaft 53, an output which corresponds with normal cyclic breathing time. The speed of the motor 51, and its output shaft 53, is regulated electrically by the rate control knob 38. The speed of the output shaft 53 will, preferably, vary from 8 to 32 rpm to accommodate patients who breathe slowly to patients who practically pant.

This output shaft 53 extends transversely across the framework 47 to be mounted therein in suitable bearings and extend from the opposite, front wall of the framework to carry a crank 54. The throw pin of the crank, in turn, is pivoted to a connecting arm 55 which extends alongside the framework and towards the cylinder 49. The extended end of the connecting arm 55 is connected to a pivot 56 which outstands from the side of the rocker R, near its center, and extends from the rocker arm R through a slot 57 in the framework 47 to the exterior of the framework.

The rocker arm R will control the distance of the piston stroke as the crank 54 rotates and this rocker arm is connected to the piston 48 by a two-piece piston rod 58. Connection of the piston rod 58 to the piston is at a lug 59 at the back of the piston. The two-piece piston rod 58 straddles this lug and is held in place by a wrist pin 60. Connection of the piston rod 58 to the rocker arm R is at a block 61 carried upon a vertical adjustment screw 62 on the rocker arm. The two-piece piston rod 58 straddles this block 61 and is held in place by a wrist pin 63, shown at FIG. 8.

The rocker R is a T-shaped member with a lateral arm 64 at its top carrying axially aligned transverse pivots 65 which fit into suitable bearings 66 at the opposite sides of the framework 47, near the top of this framework. The rocker R will thus swing about the axis of these pivots 65 and longitudinally with respect to the framework. The leg 67 of this T-shaped rocker R is offset from one side of the center plane of the unit and adjacent to the front wall of the framework 47 to permit the pivot 56 to outstand from the approximate center of this leg to extend through the slot 57 and to the connector arm 55 as heretofore described. Also, this permits the adjustment screw 62 to be carried at the center of the rocker arm, alongside the leg 67, for proper connection with the piston rod 58. This adjustment screw 62 is mounted between a top boss 68 at the center of the arm 64 and a bottom boss 69, at the bottom of the leg 67, being offset from this leg to a centered position. The upper end of the adjustment screw 62 extends through the boss 68 as a short shaft 62' which carries the volume adjustment knob 40.

Figures 4, 5, 6, 7, 8, 10, 11, 12:
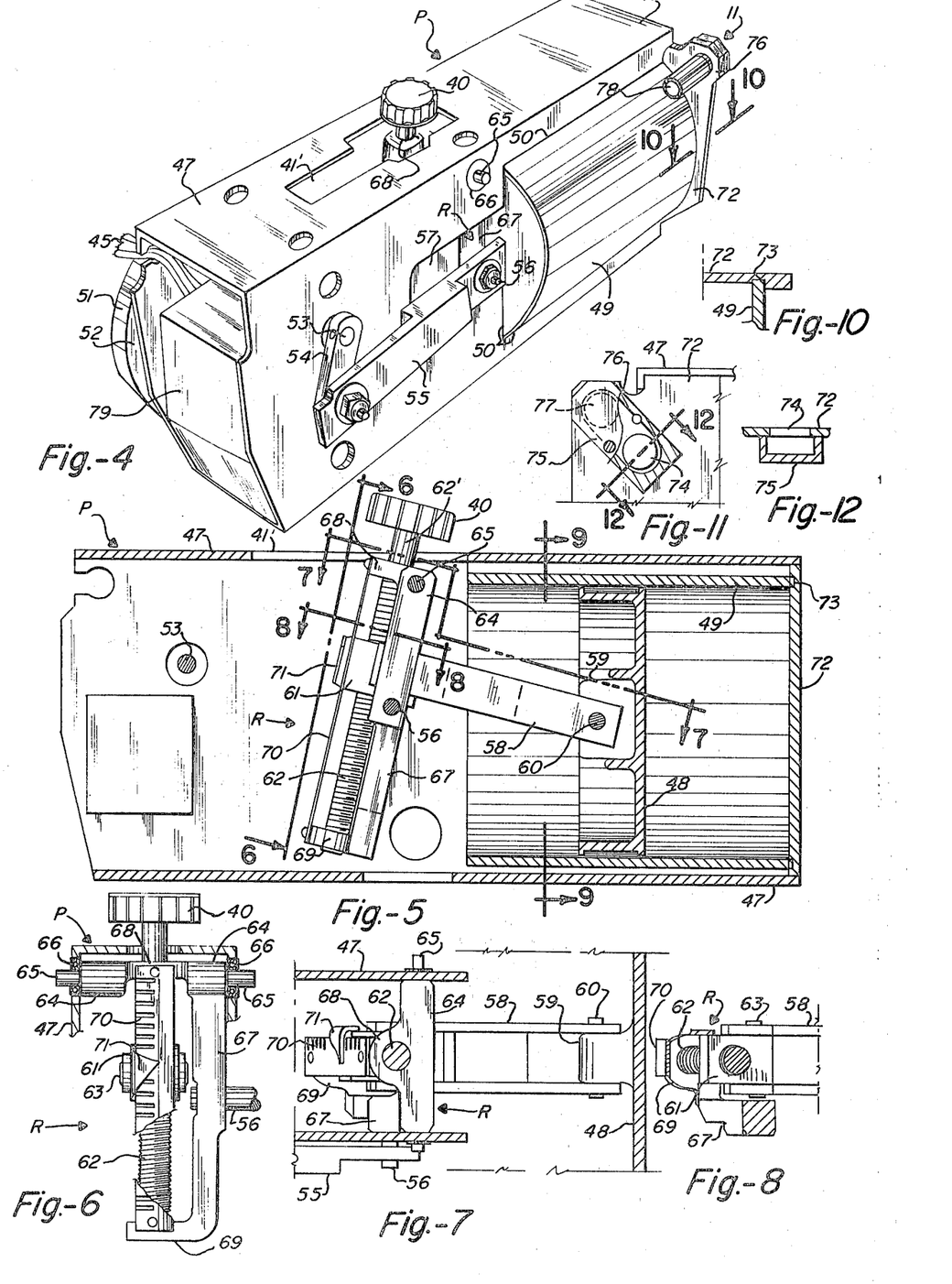
FIG. 4 is a perspective view of the pumping unit of the apparatus removed from the case.
FIG. 5 is a longitudinal sectional elevational view of the unit illustrated at FIG. 4.
FIG. 6 is a fragmentary transverse sectional detail as taken from the indicated line 6—6 at FIG. 5.
FIG. 7 is a fragmentary sectional detail as taken from the indicated line 7—7 at FIG. 5.
FIG. 8 is a fragmentary sectional detail as taken from the indicated line 8—8 at FIG. 5.
FIG. 10 is a fragmentary sectional detail as taken from the indicated line 10—10 at FIG. 4.
FIG. 11 is a fragmentary end view as taken from the indicated arrow 11 at FIG. 4, but on an enlarged scale.
FIG. 12 is a fragmentary sectional detail as taken from the indicated line 12—12 at FIG. 11.

The operation of the unit may now be described. The connecting arm 55, connected to crank 54, causes the rocker arm R to oscillate through a fixed arc established by the length of the crank 54 and the position of the pivot 56 on the rocker arm. The piston 48 reciprocates with movement of the rocker arm, with its stroke being established by the position of the block 61 on the rocker arm adjustment screw. A short stroke is with the block 61 near the top of the rocker arm; a long stroke is with the block 61 near the bottom of the rocker arm. The volume adjustment knob 40 positions the block 61, and as a matter of convenience, a gage 70 is mounted on the rocker over the adjustment screw 62 and a pointer 71 is carried upon the block 61 as shown at FIGS. 5 and 6. This permits the position of the block 61 to be calibrated to indicate various volumes of air being pumped with each stroke of the piston. The slot 41 in the cover 28 is supplemented by a corresponding slot 41' in the top of the framework 47 to permit an operator to easily see and make appropriate settings of the pointer 71.

The end of the cylinder 49 is closed by a wall plate 72 which is affixed to the framework 47 and is grooved as at 73, FIG. 10, to snugly hold the end of the cylinder. Suitable bolts or other fastening means holds this organization together. The outlet and inlet to and from the interior of this cylinder 49 is at an orifice 74 at the upper forward corner of the plate. The orifice exit at the exterior of the wall plate 72 is enclosed by a dished, diverter block 75 which is affixed to the wall plate 72 and which forms a passageway and is extended to a projected ear 76 at the upper, forward corner of the plate 72 as shown at FIGS. 4, 11 and 12. The passageway formed by this diverter block continues through an orifice 77 through the plate ear 76. A short nipple 78 projects from the surface of the plate ear at the side opposite the block 75 to lie substantially parallel with the cylinder 49.

The components above described complete the pump mechanism, excepting for suitable clips, not shown, to facilitate holding it in the case C and except for electrical components which are conveniently placed within this case such as a transformer 79 mounted in the end of the framework 47 adjacent to the output shaft 53, FIG. 4.

The cylinder 49 is operatively connected to the pressure control valve 25 by a short, flexible tube 80. This tube 80 connects with the nipple 78 and a nipple 81 on the top of the pressure control valve 25, FIG. 14. This valve 25 is a small, hollow, rectangular block which is mounted on the front wall of the case body 20 to lie within the case, but with the front face of the valve being exposed to the exterior as at a window 82 in the case wall. The pressure control valve is not only adapted to regulate pressure, but it also controls the flow of air during intake and pressure cycles of the piston. This top of the control valve 25 includes the nipple 81 and also the pressure regulation adjustment 39. The front wall of the control valve includes a second nipple 83 projecting beyond the front face window 82 for connection with the breathing tube 24.

Further, there is located at the front face of the valve 25, at the window 82, a pair of intake ports 84 which are covered by a resilient check flap 85 at the interior of the valve 25. This check flap 85 permits air to flow into the valve and through the tube 80 whenever the piston is at the intake or suction stroke, but prevents a reversal of airflow from the valve 25 at the pressure stroke of the piston. This action forces air to flow through the breathing tube 24. The expiration control valve 26, hereinafter further described, is a check valve arrangement which prevents a reverse air-flow in the breathing tube 24 during the suction stroke requiring intake air to flow through the ports 84.

Figures 15, 16, 17, 18, 19:
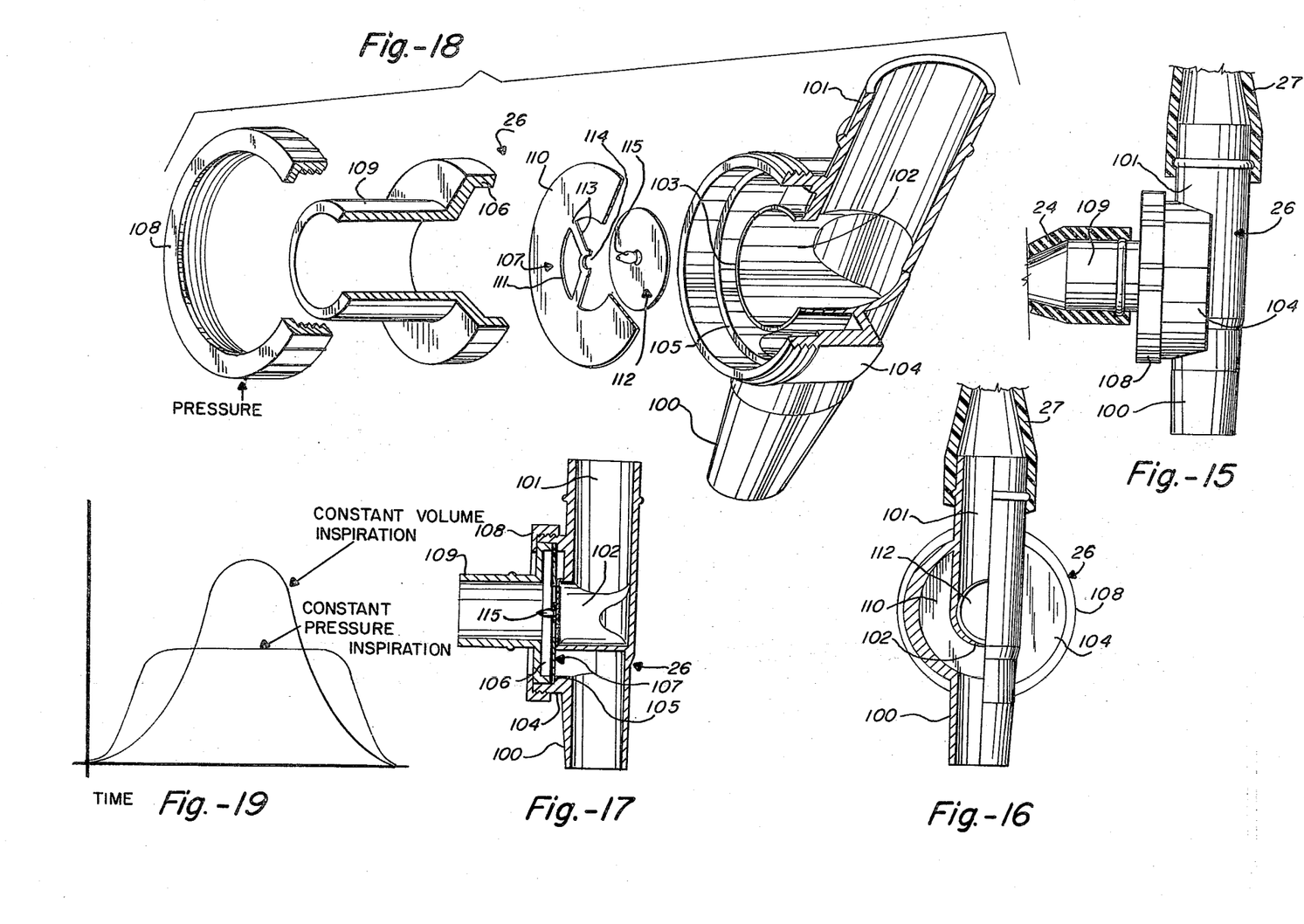
FIG. 15 is a side elevational view of the exhalation valve shown at FIG. 1, but on an enlarged scale.
FIG. 16 is a plan view of the valve shown at FIG. 15, but being partly in section to show the several components thereof.
FIG. 17 is a longitudinal sectional view of the exhalation valve.
FIG. 18 is an isometric exploded view, partly in section, to illustrate the several components of the valve.
FIG. 19 is a graph showing time-pressure relationship curves for an inspiration cycle of breathing which are possible with the apparatus.

This pressure regulation adjustment 39 is a control valve which functions to release excess pressure. This pressure regulation adjustment 39 is mounted upon a small nipple 86 upstanding from the top of the control valve 25. It is formed as a tubular body with the bottom section 87 fitting upon the nipple 86 and a concentric enlarged section 88 thereabove, with a seat 89 between the two sections. A valve disc 90 is slidably carried upon an axial rod 91 within the enlarged section to normally close against the seat 89. The rod 91 is an axial extension of a threaded shaft 92 extending through a block 93 at the top of the enlargement section 88 to connect with the pressure regulator knob 94 of the unit 39. A spring 95 about the rod 91 and between the disc 90 and the shaft 92 urges the disc against the seat 89 and the spring tension to vary the release pressure is varied by turning the knob 94 to move the shaft 92 away from or towards the seat 89. To complete the organization, vents 96 are provided in the enlarged section 88. In operation of this unit, the spring may be tightened to the point where the pump acts as a constant volume inhalation cycle, unless an unusual shut-off of the passageway occurs. An alternative type of operation provides a constant pressure inhalation cycle. The knob 94 is turned to relax the spring 95 to the point where pumping pressure will not exceed a given value. If excess pressure occurs, the disc 90 will lift away from the seat 89 to release air. These different modes of operation will produce pressure-time curves such as illustrated at FIG. 19. Some patients will require one type of positive pressure breathing and other patients will require the other.

The expiration control valve 26 should be used in conjunction with the operation of this positive pressure breathing apparatus. Otherwise, a patient will have to manipulate the mouthpiece 27 in such a manner as to close off the breathing tube 24 during the expiration cycle to prevent the same air from being pumped into his lungs during the next succeeding inspiration cycle. This can be done by tongue manipulation, but is a voluntary act and it becomes desirable to have the operation proceed automatically where the only voluntary act upon the part of the patient is to hold the breathing tube in his mouth. If necessary, the breathing tube could actually be strapped in place. The improved expiration control valve 26 was developed to meet the need for a simple, light weight valve which would have the necessary double-check valving system. On the inspiration cycle, air must flow from the breathing tube through the control valve 26 and through the mouthpiece 27. A tubular exhaust passageway 100 in this control valve must be closed off during the inspiration cycle, but air must pass from the mouthpiece 27 and through the exhaust passageway 100 during the expiration cycle. Also, the double check action must prevent air from flowing from the breathing tube 24 through the exhaust passageway 100 during the inspiration cycle and it must prevent air from flowing backwards into the breathing tube 24 during the expiration cycle.

The improved control valve 26 is shown at FIGS. 15 to 18 and includes a chambered body having the tubular exhaust passageway 100 at one end and a tubular inhalation passageway 101 at the other end, in axial alignment with the exhaust tube and connecting with the mouthpiece 27. The two sections are separated by a transverse, cylindrical inner sleeve 102 which terminates as an annular seat 103 at one side of these tube sections 100 and 101. The tubular inhalation passageway 101 communicates with the interior of the sleeve 102 while the tubular exhalation passageway 100 communicates with an annular ring 104 concentrically extended about the sleeve 102. The passageways 100 and 101, the sleeve 102 and the ring 104 are molded as a unitary piece. A shoulder 105 is formed within the ring 104 at the plane of the seat 103. A bonnet 106 fits within this sleeve and against the shoulder 105 to hold a diaphragm 107 in place. A retainer ring 108 fits over the ring 104 to hold the shoulder in place, the interior of the ring 108 and the exterior wall of the ring being threaded for a secure fit. To complete the control valve 26, a nipple 109 extends from the bonnet 106 for connection to the breathing tube 24.

The diaphragm 107, a sheet of thin, resilient material such as a selected elastomer, is mounted between the shoulder 105 and the flange 107 to bear against the seat 103. This diaphragm 107 is formed of two sections, the outer section 110 being a washer-shaped ring with a concentric opening 111 therein having a diameter slightly less than the diameter of the seat ring 103. This outer section 110 may be reinforced by thickening the material adjacent to the edge 111. An inner diaphragm 112 is mounted over this opening 111, having a diameter slightly larger than the opening 111, but smaller than the inside diameter of the seat 103. It is held in position, centered over the outer section 110 by a spider 113 of radial strips across the opening 111 and to the axial center of the unit with a small orifice 114 at this center. The inner diaphragm 112 includes a small, axially-centered spur 115 which fits into the center orifice of the spindle. This spur includes an enlarged head to lock it in the orifice 114.

Operation of the valve is as follows: During the inhalation cycle, pressure applied in the breathing tube causes the inner diaphragm 112 to lift away from the outer diaphragm 110 and permits air to flow from the breathing tube 24 and through the inhalation passageway 101. At the same time, the outer diaphragm moves against the seat 103 to prevent air from flowing through the discharge passageway 100. During the expiration cycle, the action is the opposite. The interior diaphragm 112 moves against the exterior diaphragm 110 to close off the breathing tube while the exterior diaphragm moves away from the seat 103 to provide communication between the inhalation passageway 101 and the discharge passageway 102.

I have now described my invention in considerable detail. However, it is obvious that others skilled in the art can build and devise alternate and equivalent constructions which are nevertheless within the spirit and scope of my invention. Hence, I desire that my protection be limited not by the constructions illustrated and described, but only by the proper scope of the appended claims.

What is claimed is:

1. A positive pressure respiratory apparatus to cyclically pump proper volumes of air for inspiration by a patient, as through a breathing tube extended to the patient, and comprising in combination therewith:
   a. a frame, in the general form of an elongated rectangular tube, with portions of said walls having a top wall, a bottom wall and side walls cut away to provide operative clearances and to carry the components of said apparatus as a compact unit and facilitate the implacement and removal of the components to and from a container said rectangular tube having a slot in each side wall adjacent one end of said frame and directly opposing each other;

b. a breathing tube; a cylinder having an outside diameter greater than the height of said slots and the width of said top and bottom walls and less than the height of said side walls, said cylinder being mounted within said slots and supported in said frame by said side walls, said cylinder having a closed end adjacent to one end of the frame and an open end within the frame, said breathing tube connected to and extending from the closed end and with the cylinder volume exceeding, but not greatly exceeding, the aforesaid proper volume of air for inspiration by a patient;

c. a piston within the cylinder;

d. a motor means mounted within the frame near the other end of the frame to rotate at a rate corresponding with the patient's natural or selected inspiration and exhalation breathing cycles, a crank having a first end mounted to said motor means for rotation thereof and a second end;

e. a rocker near the open end of the cylinder and having a first end pivotally mounted to the frame adjacent a sidewall of the cylinder to extend generally transversely to the cylinder and a second end and to rock towards and away from the cylinder;

f. a connecting arm having a second end pivotally mounted to the second end of said crank and a second end pivotally mounted to the second end of said crank and the rocker to swing the rocker towards and away from the cylinder as the crank rotates;

g. a piston rod pivotally connected to the rocker between said first and second ends thereof and to the piston to convert swinging movements at the rocker to sliding movements at the piston; and h. a valving means associated with the cylinder and the tube to permit air to flow into the cylinder when the piston is moving towards the open end of the cylinder and prevent a flow of air from the patient's end of the tube towards the cylinder, and to confine air flow to the tube and to the patient when the piston is moving towards the closed end of the cylinder.

2. The respiratory apparatus defined in claim 1, wherein:

the connection of the piston rod to the rocker is adjustable along the reach of the rocker to vary the stroke of the piston from a minimum stroke when the adjustable connection is adjacent to the aforesaid transverse pivot to a maximum stroke when the connection is at the opposite end of the rocker.

3. The respiratory apparatus defined in claim 2, wherein:

the rocker arm carries an adjustment screw extending substantially along the reach of the rocker and the connection of the piston rod to the rocker arm is at this adjustment screw, whereby the piston arm may be shifted along the rocker arm by rotation of the adjustment screw.

4. In the respiratory apparatus defined in claim 1, wherein the valving means includes:

a. an intake check valve means in the breathing tube adjacent to the cylinder to permit air to be drawn into the cylinder during the patient's exhalation cycle;

b. a check valve means at the patient end of the breathing tube formed as a unit having an inlet connecting to the breathing tube, a mouth outlet to be placed in the mouth of a patient, and an exhaust outlet; and c. a double-acting check within this check valve means permitting air to flow into the breathing tube inlet and through the mouth outlet, with the exhaust outlet being closed off, as during an inspiration cycle, and permitting air to flow into the mouth outlet and through the exhaust outlet, with the breathing tube inlet being closed off as during the exhalation cycle.

5. The respiratory apparatus defined in claim 4, wherein the double-acting check within the check valve means includes:

a. a first passageway from the breathing tube inlet to the exhaust outlet and a flexible diaphragm traversing and normally closing off this passageway;

b. a second passageway within the first passageway having one end normally seated on the diaphragm, at the side of the diaphragm which is opposite to the breathing tube inlet, and extending thence to the mouth outlet, whereby the seating of the diaphragm against the end of said second passageway will normally close the mouth outlet passageway to the other passageways, but pressure from the mouth outlet, as during patient exhalation, will flex the diaphragm away from the seat to provide communication between the mouth outlet and the exhaust outlet; and c. a secondary check valve at the center of the diaphragm within the embrace of the seat end of the tube inlet adapted to open responsive to pressure at the breathing tube inlet to flow air through the check valve, into the said second passageway and through the mouth outlet, as during patient inspiration, but to close responsive to a drop in pressure at the breathing tube inlet and a rise in pressure at the mouth outlet, as during exhalation.

* * * * *

UNITED STATES PATENT AND TRADEMARK OFFICE
CERTIFICATE OF CORRECTION

PATENT NO. : 4,076,021

DATED : February 28, 1978

INVENTOR(S) : Harris A. Thompson

It is certified that error appears in the above-identified patent and that said Letters Patent are hereby corrected as shown below:

Column 8, line 17, "107" should be -- 106 --.

Claim 1 should read as follows:

1. A positive pressure respiratory apparatus to cyclically pump proper volumes of air for inspiration by a patient, as through a breathing tube extended to the patient, and comprising in combination therewith:

(a) a frame having a top wall, a bottom wall and side walls in the general form of an elongated rectangular tube with portions of said walls cut away to provide operative clearances and to carry the components of said apparatus as a compact unit and facilitate the implacement and removal of the components to and from a container, said rectangular tube having a slot in each side wall adjacent one end of said frame and directly opposing each other;

(b) a breathing tube;

(c) a cylinder having an outside diameter greater than the height of said slots and the width of said top and bottom walls and less than the height of said side walls, said cylinder being mounted within said slots and supported in said frame by said side walls, said cylinder having a closed end adjacent to one end of the frame and an open end within the frame, said breathing tube connected to and extending from the closed end and with the cylinder volume exceeding, but not greatly exceeding, the aforesaid proper volume of air for inspiration by a patient;

(d) a piston within the cylinder;

(e) a motor means mounted within the frame near the other end of the frame to rotate at a rate corresponding with the patient's natural or selected inspiration and exhalation breathing cycles, a crank having a first end mounted to said motor means for rotation thereof and a second end;

(f) a rocker near the open end of the cylinder and having a first end pivotally mounted to the frame adjacent a sidewall of the cylinder and a second end to extend generally transversely to the cylinder and to rock towards and away from the cylinder;

UNITED STATES PATENT AND TRADEMARK OFFICE
CERTIFICATE OF CORRECTION

PATENT NO. : 4,076,021

DATED : February 28, 1978

INVENTOR(S) : Harris A. Thompson

It is certified that error appears in the above—identified patent and that said Letters Patent are hereby corrected as shown below:

(g) a connecting arm having a first end pivotally mounted to the second end of said crank and a second end pivotally mounted to the second end of said rocker to swing the rocker towards and away from the cylinder as the crank rotates;

(h) a piston rod pivotally connected to the rocker between said first and second ends thereof and to the piston to convert swinging movements at the rocker to sliding movements at the piston; and     (i) a valving means associated with the cylinder and the tube to permit air to flow into the cylinder when the piston is moving towards the open end of the cylinder and prevent a flow of air from the patient's end of the tube towards the cylinder, and to confine air flow to the tube and to the patient when the piston is moving towards the closed end of the cylinder.

Signed and Sealed this

Fourth Day of July 1978

[SEAL]

Attest:

RUTH C. MASON
Attesting Officer

DONALD W. BANNER
Commissioner of Patents and Trademarks